(12) United States Patent
Lisogurski (10) Patent No.: US 8,555,887 B2
(45) Date of Patent: Oct. 15, 2013

(54) TRACHEAL TUBE WITH DIVIDING MEMBRANE

(75) Inventor: Daniel Lisogurski, Boulder, CO (US)

(73) Assignee: Covidien LP, Mansfield, MA (US)

( * ) Notice: Subject to any disclaimer, the term of this patent is extended or adjusted under 35 U.S.C. 154(b) by 656 days.

(21) Appl. No.: 12/771,141

(22) Filed: Apr. 30, 2010

(65) Prior Publication Data

US 2011/0265799 A1 Nov. 3, 2011

(51) Int. Cl.
*A61M 16/00* (2006.01)
*A62B 7/00* (2006.01)

(52) U.S. Cl.
USPC ............. 128/207.15; 128/207.14; 128/204.18

(58) Field of Classification Search
USPC ............. 128/204.18, 204.21, 207.14–207.17; 604/43–45
See application file for complete search history.

(56) References Cited

U.S. PATENT DOCUMENTS

| | | | |
|---|---|---|---|
| 4,037,595 A | 7/1977 | Elam | |
| 4,077,404 A | 3/1978 | Elam | |
| 4,233,984 A * | 11/1980 | Walling | 128/207.14 |
| 4,596,246 A | 6/1986 | Lyall | |
| 4,805,612 A | 2/1989 | Jensen | |
| 5,305,740 A | 4/1994 | Kolobow | |
| 5,309,906 A * | 5/1994 | LaBombard | 128/207.14 |
| 5,713,864 A * | 2/1998 | Verkaart | 604/113 |
| 6,155,252 A * | 12/2000 | Warters | 128/200.24 |
| 6,196,222 B1 | 3/2001 | Heinonen et al. | |
| 7,275,541 B2 | 10/2007 | Fukunaga et al. | |
| 7,360,540 B2 | 4/2008 | Brain et al. | |
| 7,481,222 B2 | 1/2009 | Reissmann | |
| 7,503,325 B2 | 3/2009 | Fuhrman et al. | |
| 7,513,256 B2 | 4/2009 | Gavriely | |
| 7,617,824 B2 | 11/2009 | Doyle | |
| 7,628,789 B2 | 12/2009 | Soltesz et al. | |
| 2002/0036019 A1* | 3/2002 | Woelfel et al. | 138/115 |
| 2002/0148464 A1* | 10/2002 | Hoenig | 128/200.24 |
| 2004/0231673 A1 | 11/2004 | Reissmann | |
| 2007/0068530 A1 | 3/2007 | Pacey | |
| 2008/0078399 A1 | 4/2008 | O'Neil et al. | |
| 2008/0078401 A1 | 4/2008 | O'Neil et al. | |
| 2008/0078405 A1 | 4/2008 | Crumback et al. | |
| 2008/0236590 A1 | 10/2008 | Reissmann | |
| 2008/0257342 A1* | 10/2008 | Shiue | 128/201.28 |
| 2009/0235935 A1 | 9/2009 | Pacey | |
| 2010/0041766 A1* | 2/2010 | Smaldone et al. | 514/653 |

FOREIGN PATENT DOCUMENTS

WO 2008076628 A2 6/2008

\* cited by examiner

*Primary Examiner* — Justine Yu
*Assistant Examiner* — Rachel Young
(74) *Attorney, Agent, or Firm* — Fletcher Yoder, P.C.

(57) ABSTRACT

Various embodiments of a tracheal tube having a flexible membrane disposed therein for separation of a ventilation lumen of the tracheal tube into multiple channels are provided. The flexible membrane is configured to divide a main ventilation lumen of the tracheal tube into an inspiration channel and an expiration channel. In some embodiments, a volume of the inspiration channel is substantially equal to a volume of the expiration channel.

17 Claims, 5 Drawing Sheets

TRACHEAL TUBE WITH DIVIDING MEMBRANE

BACKGROUND

The present disclosure relates generally to medical devices and, more particularly, to airway devices, such as tracheal tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Tracheal tubes are often placed in the airway of a patient in medical situations that necessitate protection of the airway from possible obstruction or occlusion. For instance, tracheal tubes may be used in emergency situations, such as when a patient experiences cardiac or respiratory arrest. Such tracheal tubes are often coupled to an air source, such as a ventilator, to provide the patient with a source of fresh air. After patient expiration into the tracheal tube, a volume of the ventilation lumen often remains filled with expired air. Unfortunately, upon inspiration, the patient may re-breathe a portion of the expired air remaining in the ventilation lumen. Inspiration of the expired air may compromise the quality of the fresh air being supplied to the patient because the expired air may include increased carbon dioxide levels and decreased oxygen levels as compared to the fresh air supply.

Additionally, since many traditional tracheal tubes provide a single channel through which the patient inspires and expires air, biofilms may develop on an inner surface of the main ventilation lumen. Such biofilms may accumulate and even dislodge during the breathing cycle, which is generally undesirable. Accordingly, there exists a need for systems that address such drawbacks with conventional tracheal tubes.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of an endotracheal tube (ETT) having a flexible membrane disposed therein for separation of the ETT into multiple distinct channels are provided. In some embodiments, the flexible membrane is configured to divide a main ventilation lumen of the ETT into dual compartments so as to define a distinct inspiration channel and a distinct expiration channel. However, the flexibility of the membrane may facilitate movement of the membrane within the main ventilation lumen such that the volumes of the inspiration and expiration channels are substantially equal. That is, since the flexible membrane may move during operation, the volume of air inspired and expired need not be compromised by the division of the ETT into separate channels. As such, during inspiration, the foregoing features may have the effect of reducing or eliminating re-breathing of air exhaled by the patient. Furthermore, such features may reduce or eliminate biofilm growth along the length of the main ventilation lumen since air flow is established in only one direction through each channel.

The ETT may be disposable rather than reusable, capable of conveying gas to and from the patient, capable of providing separate inspiration and expiration channels without compromising the volume of airflow to and from the patient, and capable of establishing unidirectional flow through the established channels in the main lumen during intubation. As such, the devices and techniques provided herein may enable the ability to maintain a bidirectional gas flow between the patient and an external ventilation device through separate channels in the main lumen while utilizing the substantially maximum volume available in the main ventilation lumen during both inspiration and expiration cycles.

It should be noted that the provided tracheal tubes and methods of operating the tracheal tubes may be used in conjunction with auxiliary devices, such as airway accessories, ventilators, humidifiers, and so forth, which may cooperate with the tracheal tubes to maintain airflow to and from the lungs of the patient. For instance, the tracheal tubes may be placed in the trachea and coupled to a ventilator to protect the airway from possible obstruction or occlusion in emergency situations, such as when a patient experiences cardiac or respiratory arrest. For further example, the tracheal tubes may be coupled to an adapter or connector that is configured to cooperate with control circuitry to activate valving that controls the airflow to and from the patient during inspiration and expiration.

Furthermore, although the embodiments of the present invention illustrated and described herein are discussed in the context of endotracheal tubes, it should be noted that presently contemplated embodiments may include a flexible membrane disposed within a main lumen associated with any of a variety of suitable airway devices. For example, the flexible membrane may be associated with a tracheostomy tube, a Broncho-Cath™ tube, a specialty tube, or any other airway device with a main ventilation lumen. Indeed, any device with a ventilation lumen designed for use in an airway of a patient may include a flexible membrane disposed therein to divide the main lumen into multiple chambers. Furthermore, as used herein, the term "tracheal tube" may include an endotracheal tube, a tracheostomy tube, a Broncho-Cath™ tube, a specialty tube, or any other airway device.

Figure 1:
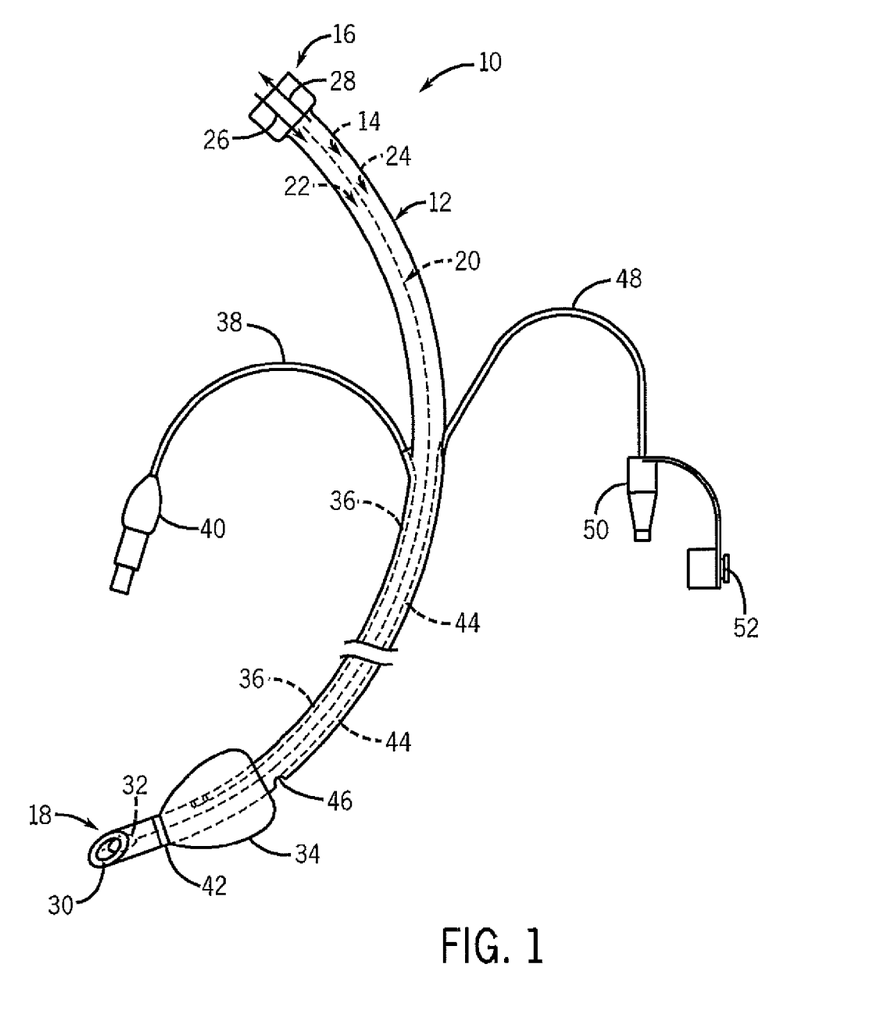
FIG. 1 is an elevational view of an exemplary endotracheal tube including a flexible membrane disposed therein in accordance with aspects of the present invention.

Turning now to the drawings, FIG. 1 is an elevational view of an exemplary tracheal tube 10 in accordance with aspects of the present disclosure. The tracheal tube 10 includes a central tubular body 12 with a main ventilation lumen 14, a proximal end 16, and a distal end 18, respectively. In some embodiments, the proximal end 14 may be outfitted with a connector that may be attached to a ventilation device during operation. The tubular body 12 also includes a flexible membrane 20 that divides the main lumen 14 into an inspiration channel 22 and an expiration channel 24. The inspiration channel 22 is configured to allow airflow to the patient, as indicated by arrow 26, and the expiration channel 24 is configured to allow airflow from the patient, as indicated by arrow 28. However, it should be noted that although the flexible membrane 20 is illustrated in a position that divides the main lumen 14 into the two channels 22 and 24, the flexible membrane 20 is adapted to move within the main ventilation lumen 14 such that the sizes of the channel 22 and the channel 24 are variable throughout operation.

The distal end 18 of the tracheal tube 10 terminates in an opening 30 and may be placed in a patient's trachea during operation to maintain airflow to and from the patient's lungs. A Murphy's eye 32 may be located on the tubular body 12 opposite the opening 30 to prevent airway occlusion when the tracheal tube assembly 10 is improperly placed within the patient's trachea. As illustrated, a cuff 34 that may be inflated to seal against the walls of a body cavity (e.g., a trachea) may be attached to the distal end 18 of the tubular body 12. The cuff 34 may be inflated via an inflation lumen 36 terminating in an inflation tube 38 connected to a fixture 40 located at the proximal end 16 of the tubular body 12. A shoulder 42 of the cuff 34 secures the cuff 34 to the tubular body 12. In some embodiments, the shoulder 42 may be folded up inside a lower end of the cuff 34 (not shown). Additionally, it should be noted that the cuff 34 may be any suitable cuff, such as a tapered cuff, a non-tapered cuff, and so forth. As illustrated, the tubular body 12 also includes a suction lumen 44 that extends from a location on the tracheal tube 10 positioned outside the body when in use to a location on the tubular body 12 below the cuff 34 and above the Murphy's eye 32. The suction lumen 44 terminates in a port 46 through which secretions may be aspirated.

An exterior suction tube 48 connects to the suction lumen 44 for the removal of suctioned fluids. The suction tube 48 terminates outside the body during use in a fixture 50 with a cap 52 that allows the suction tube 48 to be connected to auxiliary equipment (e.g., vacuum, collection reservoir, and so forth) during suctioning and to be closed when not in use. During operation, the suction tube 48 may be connected to a vacuum that applies suction in a predetermined continuous or discontinuous manner such that mucus removal is synchronized with patient expiration. For instance, vacuum may be applied such that mucus flow through the suctioning lumen 44 is established in the same direction and at the same time as airflow out of the patient through the expiration channel 24 during expiration.

The tubular body 12, the cuff 34, and the flexible membrane 20 may be formed from materials having desirable mechanical properties (e.g., puncture resistance, pin hole resistance, tensile strength, and so forth) and desirable chemical properties (e.g., biocompatibility). For example, in one embodiment, the walls of the cuff 34 may be made of a polyurethane (e.g., Dow Pellethane® 2363-80A) having suitable mechanical and chemical properties. In other embodiments, the walls of the cuff 34 may be made of a suitable polyvinyl chloride (PVC). In certain embodiments, the cuff 34 may be generally sized and shaped as a high volume, low pressure cuff that may be designed to be inflated to pressures between about 15 cm H2O and 30 cm H2O.

Likewise, the flexible membrane 20 may be made of a variety of materials having the desired flexibility and durability necessary for the given application. For example, the flexible membrane 20 may be made of materials such as silicone, polyurethane, and thin-polyvinyl chloride (PVC).

Still further, the flexible membrane 20 may include more than one layer. For instance, the flexible membrane 20 may include a structural PVC layer and a functional antimicrobial coating layer to reduce or eliminate undesirable microbial growth. The flexible membrane 20 may also be composed of multiple structural layers that each endows the membrane with desirable properties. For example, the flexible membrane 20 may include one layer that imparts the membrane with durability and one layer that imparts the membrane with flexibility. Still further, the flexible membrane may include elastic materials, which allow the membrane to move within the main lumen of the tracheal tube during intubation of a patient.

During operation, the tracheal tube 10 is inserted into the trachea of a patient, often while the patient is resting in a typical semirecumbent position. After insertion, the cuff 34 may be inflated via a syringe connected to the inflation tube 38, thus holding the tracheal tube 10 in position. During use, when the cuff 34 is inflated and the tracheal tube 10 is placed such that it is centered within the trachea, the port 46 may be utilized to aspirate secretions accumulating above the cuff 34. Furthermore, the flexible membrane 20 is adapted to move within the main lumen 14 to enlarge the inspiration channel 22 when the patient is receiving air and to enlarge the expiration channel 24 when the patient is exhaling air. As such, separate channels are utilized by the patient during inspiration and expiration.

Figure 2:
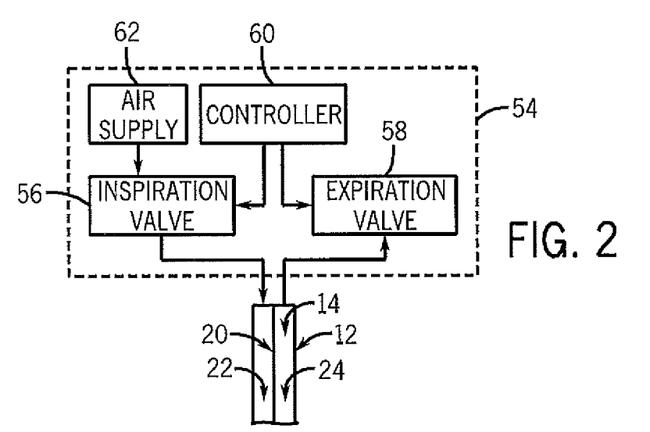
FIG. 2 is a schematic illustrating an exemplary ventilation system coupled to a tracheal tube ventilation lumen that is divided into an expiration channel and an inspiration channel by a flexible membrane.

FIG. 2 is a schematic illustrating an exemplary ventilation system 54 coupled to the tracheal tube body 12 via the main lumen 14, which is divided into the expiration channel 24 and the inspiration channel 22 by the flexible membrane 20. In the illustrated embodiment, the ventilation system 54 includes an inspiration valve 56 coupled to the inspiration channel 22 and an expiration valve 58 coupled to the expiration channel 24. The inspiration valve 56 and the expiration valve 58 are coupled to a controller 60 that is configured to output one or more control signals to direct the operation of the valves 56 and 58. The inspiration valve 56 is also connected to an air supply 62 that provides a fresh gas mixture to the patient during inspiration.

It should be noted that the inspiration valve 56, the expiration valve 58, and the controller 60 may be located in the ventilator 54 as shown in FIG. 2 or may be positioned in a standalone unit. That is, in some embodiments, such components may be separate from the ventilator 54 such that existing systems may be retrofitted with a desirable valve system. Still further, certain embodiments of the tracheal tube with the dividing membrane disclosed herein may not be coupled to an external valve system. In such embodiments, the valve system internal to or coupled to the tracheal tube itself may provide adequate valving for the given application. Indeed, the tracheal tubes disclosed herein may be coupled to an external valve system, may have a valve system integral in the tube itself, or may have no valve system at all.

During operation, the ventilation system 54 is configured to output a fresh gas mixture to the patient and receive exhaled air from the patient. For example, at the beginning of an inspiration cycle, the air supply 62 is adapted to output a fresh gas mixture to the inspiration valve 56, which is directed to open by the controller 60. A fresh gas mixture flows through the inspiration valve 56 to the inspiration channel 22. As the fresh gas mixture flows into the inspiration channel 22, the flexible membrane 20 adjusts to enlarge the inspiration channel 22 and allow the incoming air to flow to the patient. At the completion of the inspiration cycle, the expiration cycle is initiated. As such, the controller 60 directs the inspiration valving 56 to close and directs the expiration valving 58 to open. As the patient exhales, the air flow from the patient causes the flexible membrane 20 to alter its position to enlarge the expiration channel 24. The exhaled air is then either received by the ventilation device 54 and expelled from the ventilation device 54 or is expelled directly into the surrounding environment. In such a way, the valving may be utilized to ensure that inhaled air travels exclusively through the inspiration channel 22 and exhaled air travels exclusively through the expiration channel 24. Indeed, any of a variety of suitable valving arrangements may be employed in conjunction with the tracheal tube with a flexible membrane. For example, the valving may include one way valves, two way valves, reversing valves, and so forth, as desired for the given embodiment.

Figure 3:
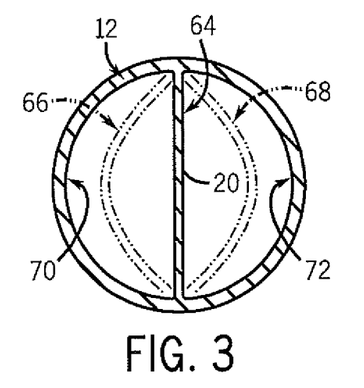
FIG. 3 is a cross sectional view of the tracheal tube of FIG. 1 illustrating an embodiment of an elastic flexible membrane.

FIG. 3 is a cross sectional view of the tracheal tube 10 of FIG. 1 illustrating an embodiment of the flexible membrane 20 during use. As shown, the flexible membrane 20 may default to a first position 64 during intubation of the patient. Subsequently, during use, the flexible membrane 20 may flex to a second position 66 and/or a third position 68 as the patient breathes in and out. For example, in the illustrated embodiment, the membrane 20 may be made of a substantially elastic material that is adapted to stretch between the second position 66 and the third position 68 during the breathing cycle. Still further, in other embodiments, the membrane 20 may be configured to stretch or flex to a variety of other positions not indicated in FIG. 3. For instance, the membrane 20 may flex to a position beyond position 66 further toward wall 70 to enlarge an inspiration channel when air is flowing into the patient's lungs. The membrane 20 may then flex to a position beyond position 68 further toward wall 72 to enlarge an expiration channel when the patient is exhaling.

In some embodiments, the flexible membrane 20 may be configured to stretch to a maximum position equal to approximately half the circumference of the inner diameter of the main lumen of the tracheal tube. That is, the membrane 20 may be adapted to stretch to a maximum position such that the membrane 20 lies flat against the wall 70 or 72 when stretched. Still further, in other embodiments, the membrane 20 may be configured to stretch to a position equal to less than half the circumference of the inner diameter of the main lumen such that the membrane 20 does not contact either of the lumen walls 70 and 72. Indeed, the flexible membrane 20 may be configured to stretch to any suitable length so as to define a separate inspiration channel and a separate expiration channel during the breathing cycle.

Figure 4:
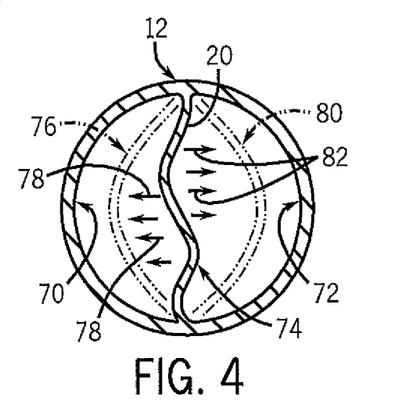
FIG. 4 is a cross sectional view of the tracheal tube of FIG. 1 illustrating an embodiment of a flexible membrane including slack.

FIG. 4 is a cross sectional view of the tracheal tube 10 of FIG. 1 illustrating a further embodiment of the flexible membrane 20 during use. In this embodiment, the default position 74 of the membrane 20 is not taut as in the embodiment of FIG. 3, but rather includes a looser structure. As such, in this embodiment, the membrane 20 may not be elastic since the default position 74 of the membrane 20 includes enough slack to allow for movement from side to side within the main lumen of the tracheal tube 12. During operation, in one embodiment, the membrane 20 may move from position 74 toward outer wall 70 to position 76 during patient inspiration, as indicated by arrows 78, to define a distinct inspiration channel. Similarly, the membrane 20 may move from position 74 to position 80 during patient expiration, as indicated by arrows 82, to define a distinct expiration channel. As such, the length of the flexible membrane 20 may be greater than or equal to the inner diameter of the main ventilation lumen. For example, in some embodiments, the length of the membrane 20 may be between the inner diameter of the main ventilation lumen and the circumference of the ventilation lumen. As such, the flexible membrane 20 is adapted to move within the main lumen to separately define an inspiration channel and an expiration channel each with a volume that is approximately equal to the volume of the main ventilation lumen. Such a feature may offer distinct advantages over airway devices that separate the volume of the main lumen, thereby reducing the volume available for airflow during each phase of the respiration cycle.

Figure 5:
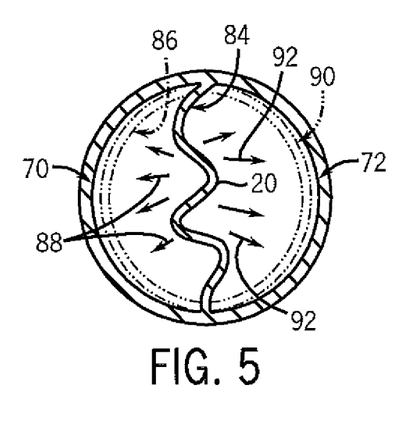
FIG. 5 is a cross sectional view of the tracheal tube of FIG. 1 illustrating an embodiment of a flexible membrane including slack.

FIG. 5 is a cross sectional view of the tracheal tube 10 of FIG. 1 illustrating a further embodiment of the flexible membrane 20 during use. In this embodiment, the flexible membrane 20 is substantially longer than the flexible membrane of FIG. 4. As shown, during inspiration, the membrane 20 may flex outward toward wall 70 to position 86, as indicated by arrows 88, to define an inspiration channel. In this embodiment, the length of the membrane 20 is such that when the membrane 20 is in position 86, the membrane 20 is substantially close to wall 70. Indeed, in some embodiments, the membrane 20 may be contacting the wall 70. Likewise, during operation, the membrane 20 may flex toward the wall 72 from position 84 to position 90, as indicated by arrows 92. Furthermore, as the patient alternates between inspiration and expiration, the membrane 20 may flex between position 86 and position 90. Again, the length of the membrane 20 is such that when the membrane is in position 90 the membrane 20 is substantially close to the wall 72 and may be in contact with the wall 72 in some embodiments. Additionally, it should be noted that the membrane may be both elastic, as in the embodiment of FIG. 3, and may have slack, as in the embodiments of FIGS. 4 and 5.

Figure 6:
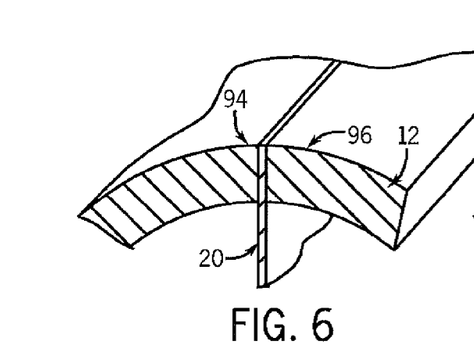
FIG. 6 illustrates an exemplary adhesion attachment mechanism between a wall of a tracheal tube and an exemplary flexible membrane.

FIG. 6 illustrates an exemplary attachment between the wall of the tracheal tube 12 and the flexible membrane 20. In this embodiment, the membrane 20 is adhered to a first side 94 of the tracheal tube 12 and a second side 96 of the tracheal tube 12. That is, the membrane 20 may be glued or stuck via an alternative adhesive to the first side 94 and the second side 96 of the tracheal tube 12. In such an arrangement, the flexible membrane 20 may be embedded in the wall of the tracheal tube 12 such that during the breathing cycle as the patient inhales and exhales, a middle section of the membrane 20 is configured to move within the main lumen while the end portions of the membrane 20 remain fixed as shown in FIG. 6.

Figure 7:
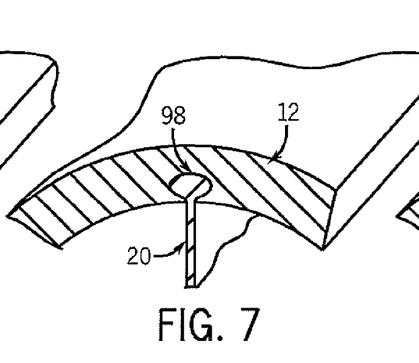
FIG. 7 illustrates an exemplary protrusion and groove attachment mechanism between a wall of a tracheal tube and an exemplary flexible membrane.

FIG. 7 illustrates an alternate exemplary attachment mechanism that may be used to secure the flexible membrane 20 to the wall of the tracheal tube 12. In this embodiment, the membrane 20 includes a protrusion 98 that is embedded in the tracheal tube wall 12 during use. A width of the protrusion 98 is greater than a width of the membrane 20 located within the main lumen. As such, the protrusion 98 remains embedded in the tracheal tube wall 12 as the membrane flexes and moves during the breathing cycle of the patient. That is, the protrusion 98 substantially prevents the membrane 20 from dislodging from the tracheal tube wall 12 during operation. In some embodiments, the protrusion 98 may fit into a groove that is pre-formed in the tracheal tube wall 12.

Figure 8:
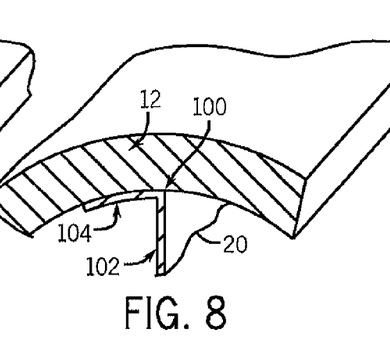
FIG. 8 illustrates an exemplary adhesion attachment mechanism between a wall of a tracheal tube and an exemplary flexible membrane.

FIG. 8 illustrates another exemplary attachment mechanism that may be utilized to secure the flexible membrane 20 to the tracheal tube wall 12. In this embodiment, the flexible membrane 20 includes a fold 100 located between a first portion 102 of the membrane 20 and a second portion 104 of the membrane 20. The second portion 104 of the membrane 20 is adhered to the tracheal tube wall 12 to secure the membrane 20 to the tracheal tube during use. As such, the first portion 102 of the membrane 20 may flex and move to selectively define an inspiration channel and an expiration channel as the patient inhales and exhales. It should be noted that the adhesion of the second portion 104 of the membrane 20 to the tracheal tube wall 12 may be reversed. That is, the fold 100 may be reversed such that an opposite surface of the second portion 104 is adhered to the tracheal tube wall 12. For example, in one embodiment, the second portion 104 of the membrane 20 located on one side of the tracheal tube may be positioned in a first direction, and a second portion of the membrane 20 located on the opposite side of the tracheal tube may be positioned in the opposite direction.

Figure 9:
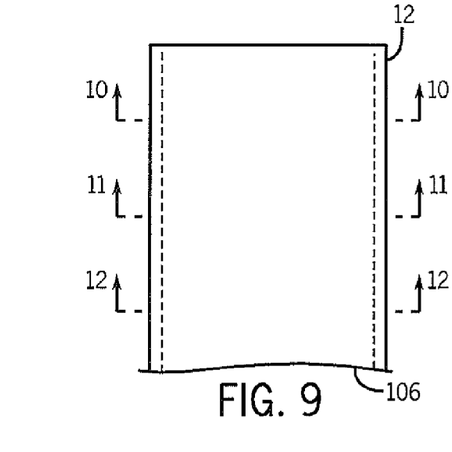
FIG. 9 is a cross sectional view of an exemplary tracheal tube with a variable tensioned flexible membrane mounted therein.

FIG. 9 is a cross sectional view of an exemplary tracheal tube with a variable tensioned flexible membrane 106 mounted therein. The variable tensioned flexible membrane 106 includes different tension levels lengthwise along the membrane. That is, in some areas along the length of the membrane 106, the tension may be tighter while in other areas along the length of the same membrane, the tension may be looser. An exemplary variation of the tension along the length of the membrane 106 is illustrated in the cross sections take along lines 10-10, 11-11, and 12-12 of FIG. 9.

Figure 10:
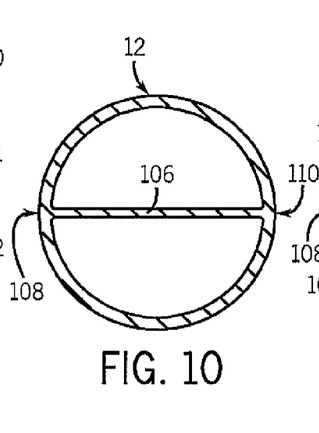
FIG. 10 is a sectional view through the tracheal tube of FIG. 9 illustrating a tension level of the flexible membrane at a first exemplary position along the length of the flexible membrane.
Figures 11, 12:
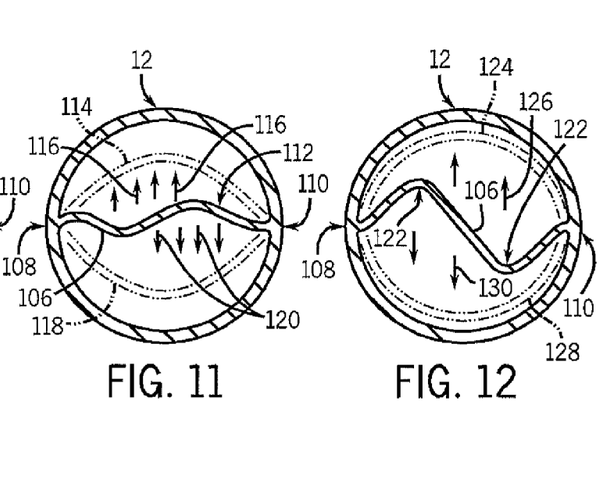
FIG. 11 is a sectional view through the tracheal tube of FIG. 9 illustrating a tension level of the flexible membrane at a second exemplary position along the length of the flexible membrane.
FIG. 12 is a sectional view through the tracheal tube of FIG. 9 illustrating a tension level of the flexible membrane at a third exemplary position along the length of the flexible membrane.

Specifically, FIG. 10 illustrates a section of the variable tension membrane 106 taken along line 10-10 of FIG. 9. At this lengthwise position along the membrane 106, the membrane 106 is taut and no slack exists from a first side 108 of the tracheal tube body 12 to a second side 110 of the tracheal tube body 12. As such, the tension at such a position in the flexible membrane 106 is high relative to the positions at further distances along the membrane 106. For example, FIG. 11 illustrates a section of the variable tension membrane 106 taken along line 11-11 of FIG. 9. At this lengthwise position along the membrane 106, the membrane 106 includes slack 112 in the direction from side 108 to side 110 of the tracheal tube 12 such that the membrane 106 may expand outward toward the walls of the tracheal tube 12. For example, the membrane 106 may include enough slack to expand outward toward position 114, as indicated by arrows 116, and to expand outward toward position 118, as indicated by arrows 120. For further example, the slack 112 in the membrane 106 may allow the membrane to flex to position 114 to define an inspiration channel and to position 118 to define an expiration channel.

FIG. 12 illustrates another section of the variable tension membrane 106 taken along line 12-12 of FIG. 9. At this lengthwise position along the membrane 106, the membrane 106 includes additional slack 122 relative to the position illustrated in FIG. 11. As such, the membrane 106 is configured to flex outward to a position 124, as indicated by arrows 126, and to a position 128, as indicated by arrows 130, during use in a breathing cycle. For example, the membrane 106 may flex to position 124 during inspiration to define an inspiration chancel and to position 128 during expiration to define an expiration channel. As such, the variable tensioned membrane 106 may include different tension and slack levels at various positions along the length of the membrane 106.

Figure 13:
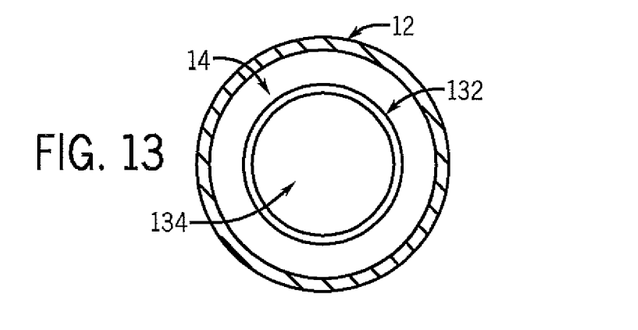
FIG. 13 is a cross sectional view of an embodiment of a tracheal tube including a circular flexible membrane disposed within a main lumen of the tracheal tube to separate the main lumen into an inspiration channel and an expiration channel.

FIG. 13 is a cross sectional view of another embodiment of the tracheal tube 12 including a flexible membrane configured to define an inspiration channel and an expiration channel. In this embodiment, the tracheal tube 12 includes a circular flexible membrane 132 disposed within the main lumen 14 of the tracheal tube 12. In the illustrated embodiment, the circular membrane 132 is shown in an expanded orientation such that an inspiration channel 134 is established within the main lumen 14 of the tracheal tube 12. That is, the circular membrane 132 may be configured to expand and collapse to define distinct inspiration and expiration channels during the breathing cycle. For example, the circular membrane 132 may be configured to collapse in on itself during expiration and expand toward the inner walls of the main lumen 14 during inspiration. Still further, in other embodiments, the circular membrane 132 may include additional modifications that facilitate the separation of the main lumen 14 into distinct channels during the breathing cycle.

Figure 14:
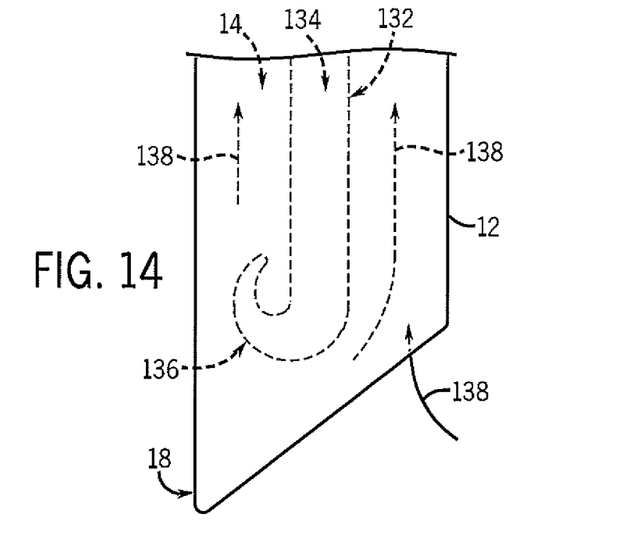
FIG. 14 is a cross sectional view of the tracheal tube of FIG. 13 illustrating a curled portion of the circular flexible membrane during expiration.

FIG. 14 illustrates an exemplary modification that may be made to the circular membrane 132 of FIG. 13 near the distal end 18 of the tracheal tube 12 to facilitate inspiration and expiration through separate channels established in the tracheal tube 12. As illustrated, a distal end of the circular membrane 132 includes a curled portion 136 that is configured to remain curled (i.e., in a closed position that prevents airflow through the circular membrane) during expiration. Accordingly, as shown, during patient expiration, airflow is established in an outward direction, as indicated by arrows 138 through the main lumen 14 without entering the circular membrane 132.

Figure 15:
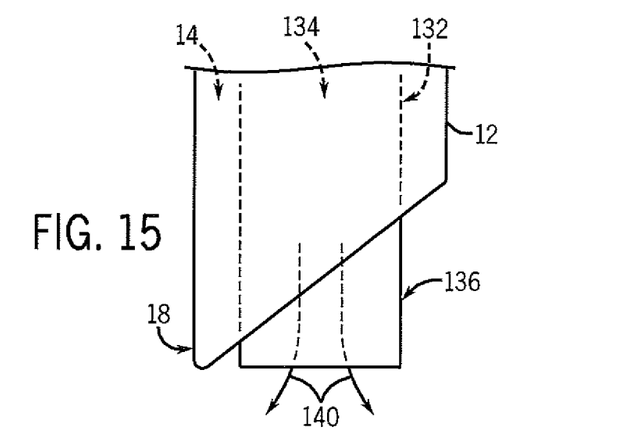
FIG. 15 is a cross sectional view of the circular flexible membrane of FIG. 13 illustrating a curled portion of the circular flexible membrane during inspiration.

FIG. 15 illustrates positioning of the curled end 136 of the circular membrane 132 during patient inspiration. As shown, the curled end 136 uncurls to allow air to flow to the patient through the inspiration channel 134 in the direction indicated by arrows 140. That is, the curled end 136 is configured to curl and uncurl in accordance with the breathing cycle to define an inspiration channel through the circular membrane 132 or an expiration channel through the main lumen 14. When the curled end 136 is in a curled position, air is prohibited from flowing through the inspiration channel 134. However, during inspiration, pressurized airflow, such as air from a ventilation device, may force the curled end 136 to uncurl, thus allowing air to flow to the patient. In this way, the circular membrane 132 disposed in the main lumen 14 may be utilized to define a separate inspiration channel and a separate expiration channel during the breathing cycle of a patient.

It should be noted that the width of the flexible membrane disposed in the tracheal tube may be greater than, less than, or equal to the inner diameter of the main lumen of the tracheal tube. Indeed, in some embodiments, the width of the flexible membrane may be equal to the inner diameter of the main lumen in some areas, less than the inner diameter of the main lumen in other areas, and greater than the inner diameter of the main lumen in additional areas. FIGS. 16 through 20 illustrate a variety of possible widths of the flexible membrane with respect to the inner diameter of the tracheal tube.

Figure 16:
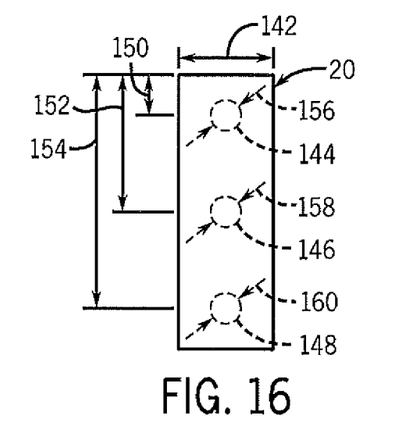
FIG. 16 illustrates an exemplary flexible membrane in which the width of the flexible membrane is substantially equal to an inner diameter of a main lumen of the tracheal tube.

FIG. 16 illustrates an exemplary flexible membrane 20 in which the width of the flexible membrane 20 is substantially equal to an inner diameter 142 of the main lumen of the tracheal tube. The illustrated flexible membrane 20 includes a plurality of ports 144, 146, and 148 disposed lengthwise along the flexible membrane 20. The first port 144 is disposed at a first distance 150 from the end of the flexible membrane 20, the second port 146 is disposed at a second distance 152 from the end of the flexible membrane 20, and the third port 148 is disposed at a third distance 154 from the end of the flexible membrane 20. It should be noted that the distances 150, 152, and 154 may be any suitable distances such that the ports 144, 146, and 148 are located in the desired positions. For example, the ports 144, 146, and 148 may be equidistantly spaced relative to one another as shown in the illustrated embodiment.

In the illustrated embodiment, the ports 144, 146, and 148 are defined by diameters 156, 158, and 160, respectively. The diameters 156, 158, and 160 may be substantially equal or may be different as desired. For example, it may be desirable to provide a plurality of large ports and a plurality of small ports advantageously located at varying positions along the length of the flexible membrane 20. The ported flexible membrane may offer a variety of distinct advantages over non-ported membranes. For example, the ported membrane may allow air to flow from one side of the membrane to the other side of the membrane during operation, thereby facilitating the transition between the inspiration channel and the expiration channel throughout the breathing cycle. For further example, the ports may render the flexible membrane "leaky" such that inspiration air may permeate to the expiration side of the membrane. Such a membrane may substantially isolate the expiration and inspiration channels from one another while allowing minimal airflow across the membrane.

Figure 17:
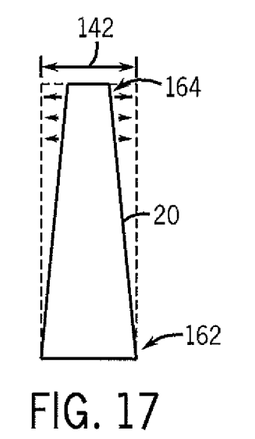
FIG. 17 illustrates an embodiment of an exemplary flexible membrane in which a first end of the flexible membrane is substantially wider than a second end of the flexible membrane.

FIG. 17 illustrates an alternate embodiment of the flexible membrane 20 in which a first end 162 of the flexible membrane 20 is substantially wider than a second end 164 of the flexible membrane 20. That is, in the illustrated embodiment, the second end 164 of the flexible membrane 20 is not as wide as the inner diameter 142 of the main lumen. Indeed, along the length of the flexible membrane 20 from the first end 162 to the second end 164, the width of the flexible membrane 20 varies. As such, portions of the flexible membrane 20 are as wide as the inner diameter 142 of the lumen and other portions are not as wide as the lumen.

Figure 18:
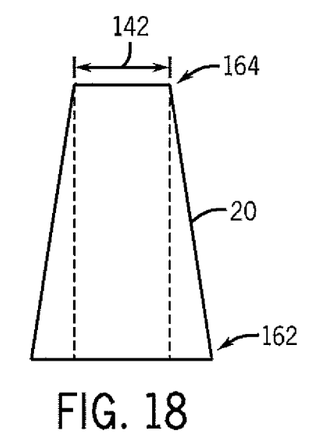
FIG. 18 illustrates an embodiment of an exemplary flexible membrane in which a width of the flexible membrane is greater than an inner diameter of a main lumen of a tracheal tube.

FIG. 18 illustrates another embodiment of the flexible membrane 20 in which a width of the flexible membrane 20 is greater than the inner diameter 142 of the main lumen. That is, at the first end of the flexible membrane 20, a width of the flexible membrane 20 is substantially wider than the inner diameter 142. The width of the flexible membrane 20 decreases lengthwise from the first end 162 to the second end 164 until the width of the flexible membrane 20 is equal to the inner diameter 142 at the second end 164. That is, in some embodiments, the width of the flexible membrane 20 may exceed the inner diameter 142 of the main lumen of the tracheal tube. It should be noted that the width of the flexible membrane 20 may vary in a variety of ways not illustrated in FIG. 18. For example, the width of the membrane may be substantially equal to the inner diameter of the main lumen at the first end 162 of the membrane and may be greater than the inner diameter of the main lumen at the second end 164 of the membrane. Furthermore, in some embodiments, the flexible membrane 20 may be configured to seal against a wall of the tracheal tube, thereby functioning as a valve that facilitates the separation of the tracheal tube into an inspiration channel and an expiration channel during the breathing cycle of the patient.

Figure 19:
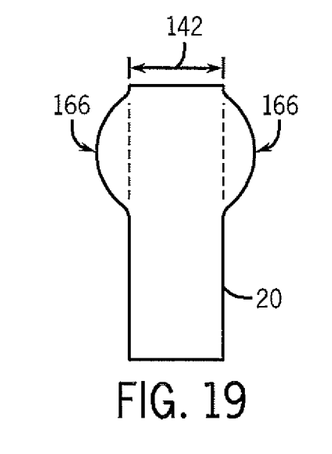
FIG. 19 illustrates an embodiment of an exemplary flexible membrane including an expanded portion that extends outward beyond an inner diameter of a ventilation lumen of a tracheal tube.
Figure 20:
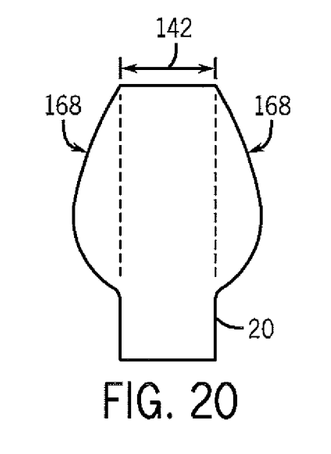
FIG. 20 illustrates an embodiment of an exemplary flexible membrane including an expanded portion that extends outward beyond an inner diameter of a ventilation lumen of a tracheal tube.

FIG. 19 illustrates another embodiment of the flexible membrane 20 including an expanded portion 166 that extends outward beyond the inner diameter 142 of the inner lumen. Similarly, FIG. 20 illustrates an alternate embodiment of the flexible membrane 20 including an expanded portion 168 that is greater in width than the inner diameter 142 of the main lumen. Indeed, the expanded portions 166 and 168 may be elongated as in FIG. 20 or shortened as in FIG. 19 and may extend along the entire length of the flexible membrane 20 or only a portion of the membrane 20.

It should be noted that features of the embodiments illustrated in FIGS. 16-20 may be combined in some embodiments of the flexible membrane. For example, the porosity of the membrane of FIG. 16 may be combined with the expanded portions of the embodiment of FIG. 19. Indeed, an embodiment of the flexible membrane may include any combination of the features of the illustrated membranes, such as expanded portions, pores, sections wider than an inner diameter of the main lumen, sections narrower than the inner diameter of the main lumen, and so forth.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube, comprising:
 a tubular body having an open distal end and a ventilation lumen for ventilating a patient; and
 a flexible membrane disposed within the ventilation lumen of the tubular body and configured to move or flex to define an inspiration channel and an expiration channel during a breathing cycle of the patient, wherein the flexible membrane is a variable tensioned membrane comprising a first portion with a first tension level and a second portion with a second tension level, wherein the first tension level is substantially different from the second tension level.

2. The tracheal tube of claim 1, wherein the flexible membrane is formed from at least one of silicone, polyurethane, and thin-polyvinyl chloride (PVC).

3. The tracheal tube of claim 1, wherein the tracheal tube is configured to be attached to at least one of a ventilator, a bag for ventilation, inspiration valving, expiration valving, and an air supply.

4. The tracheal tube of claim 1, wherein a transverse length of the flexible membrane is less than or equal to one half of the circumference of the ventilation lumen.

5. The tracheal tube of claim 1, wherein a transverse length of the flexible membrane is greater than one half of the circumference of the ventilation lumen.

6. The tracheal tube of claim 1, wherein the flexible membrane comprises a protrusion, the tubular body comprises a groove, and the flexible membrane is coupled to the tubular body via the protrusion fitting in the groove.

7. The tracheal tube of claim 1, wherein a first end portion of the flexible membrane is embedded within a first portion of a wall of the tubular body and a second end portion of the flexible membrane is embedded within a second portion of the wall of the tubular body.

8. The tracheal tube of claim 1, wherein the variable tensioned membrane gradually increases from the first tension level to the second tension level lengthwise along the tubular body.

9. The tracheal tube of claim 1, wherein the flexible membrane comprises one or more pores configured to allow airflow from a first side of the membrane to a second side of the membrane.

10. A tracheal tube, comprising:
 a tubular body having an open distal end and a main lumen for ventilating a patient; and
 a membrane disposed within the main lumen of the tubular body and configured to alternate between a first position and a second position to define an inspiration channel and an expiration channel during a breathing cycle of the patient, wherein the membrane is a variable tensioned membrane comprising a first portion with a first tension level and a second portion with a second tension level, wherein the first tension level is substantially different from the second tension level.

11. The tracheal tube of claim 10, wherein the membrane comprises an antimicrobial layer.

12. The tracheal tube of claim 10, wherein the membrane is configured to allow air to permeate from the inspiration channel to the expiration channel during the breathing cycle.

13. The tracheal tube of claim 10, comprising a valve disposed at a proximal end of the membrane and configured to enable the flow of air to the patient during the patient inspiration.

14. A tracheal tube, comprising:
 a tubular body having an open distal end and a ventilation lumen for ventilating a patient;
 a cuff disposed around the tubular body above the open distal end and configured to be inflated to seal the cuff against a wall of a trachea of a patient; and
 a membrane disposed within the ventilation lumen of the tubular body and configured to flex to define an inspiration channel and an expiration channel during a breathing cycle of the patient, wherein the width of the membrane gradually increases along the length of the membrane.

15. The tracheal tube of claim 14, wherein the membrane is configured to be attached to inspiration valving and expiration valving, and wherein the inspiration valving and the expiration valving cooperate to allow airflow in a first direction to the patient during inspiration and in a second direction from the patient during expiration.

16. The tracheal tube of claim 14, wherein the width of the membrane gradually increases from a width equal to an inner diameter of the ventilation lumen to a width greater than the inner diameter of the ventilation lumen.

17. The tracheal tube of claim 14, wherein the membrane is a variable tensioned membrane comprising a first portion with a first tension level and a second portion with a second tension level, wherein the first tension level is substantially different from the second tension level.

* * * * *